(12) United States Patent
Chen et al.

(10) Patent No.: US 7,314,972 B2
(45) Date of Patent: Jan. 1, 2008

(54) TRANSGENIC PLANTS EXPRESSING BIOCIDAL PROTEINS AND METHOD OF PRODUCING THE SAME

(75) Inventors: Ching-San Chen, Taipei (TW); Gan-Hong Chen, Tainan County (TW); Li-Wen Lo, Taipei County (TW)

(73) Assignee: Academia Sinica, Taipei (TW)

( * ) Notice: Subject to any disclaimer, the term of this patent is extended or adjusted under 35 U.S.C. 154(b) by 268 days.

(21) Appl. No.: 11/057,717

(22) Filed: Feb. 14, 2005

(65) Prior Publication Data

US 2005/0204420 A1    Sep. 15, 2005

Related U.S. Application Data

(60) Continuation-in-part of application No. 10/409,818, filed on Apr. 8, 2003, now Pat. No. 7,091,312, which is a division of application No. 09/686,332, filed on Oct. 11, 2000, now Pat. No. 6,653,463.

(51) Int. Cl.
  *C12N 15/09* (2006.01)
  *C12N 15/82* (2006.01)
  *A01H 5/00* (2006.01)

(52) U.S. Cl. .................. 800/279; 800/278; 800/298; 800/295; 800/320.1; 800/320.2; 800/317; 800/317.3; 435/468; 435/419; 435/430.1

(58) Field of Classification Search ............... 800/279
See application file for complete search history.

(56) References Cited

OTHER PUBLICATIONS

Lazar et al. Molecular and Cellular Biology, Mar. 1988, vol. 8, No. 3, pp. 1247-1252.*
Broun et al. Science, Nov. 13, 1998, vol. 282, pp. 1315-1317.*
Bloch et al., "A New Family of Small (5 kDa) Protein Inhibitors of Insect α-amylases From Seeds or Sorghum (Sorghum bicolor (L) Moench) Have Sequence Homologies With Wheat γ-Purothionins", , FEBS Letters, vol. 279, No. 1, pp. 101-104 (1991).
Carlini et al., "Biological Effects of Canatoxin in Different Insect Models: Evidence for A Proteolytic Activation of the Toxin by Insect Cathepsinlike Enzymes", J. Econ Entomol 90: 340-348 (1997).
Ferreira et al., "Proteolytic Activation of Canatoxin, a Plant Toxic Protein, by Insect Cathepsin-Like Enzyme," Arch Insect Biochem Physiol 44: 162-171 (2000).
Froy et al., "Membrane Potential Modulators: A Thread of Scarlet From Plants to Humans," The FASEB Journal, vol. 12, No. 15, pp. 1793-1796 (1998).
Ghazaleh et al., "Stimulation of Calcium Influx and Platelet Activation by Canatoxin: Methoxyverapamil Inhibition and Downregulation by cGMP," Arch Biochem Biophys 339: 362-367 (1997).
Hilder et al., "Protein and cDNA Sequences of Bowman-Birk Protease Inhibitors From the Cowpea (*Vigna unguiculata* Walp.)", Plant Molecular Biology, vol. 13, No. 6, pp. 701-710 (1989).
Ishimoto et al., "Protective Mechanism of the Mexican Bean Weevil Against High Levels of Alpha-Amylase Inhibitor in the Common Bean," Plant Physiol 111: 393-401(1996).
Ishimoto et al., "Insecticidal Activity of an α-amylase Inhibitor-like Protein Resembling a Putative Precursor of α-amylase Inhibitor in the Common Bean, Phaseolus Vulgaris L," Biochemica Biophysica Acta, pp. 104-112 (1999).
Janzen et al "Insecticidal Action of the Phytohemagglutinin in Black Beans on a Bruchid Beetle," Science 192: 795-796 (1976).
Kaga et al., "Genetic Localization of a Bruchid Resistance Gene and Its Relationship to Insecticidal Cyclopeptide Alkaloids, the Vignatic Acids, in Mungbean (*Vigna Radiata* L. Wilczek)," Molecular & General Genetics, vol. 258, No. 3, pp. 378-384 (1998).
Koiwa et al., "Phage Display Selection Can Differentiate Insecticidal Activity of Soybean Cystatins Plan" J 14: 371-379 (1998).
Kornegay et al., "Inheritance of resistant to Mexican Bean Weevilin Common Bean, Determined by Bioassay and Biochemical Tests," Crop Sci 33: 589-594 (1993).
Macedo et al., "Purification and Properties of Storage Proteins (vicilins) from Cowpea (*Vigna unguiculata*) Seeds Which are Susceptible or Resistant to the Bruchid Beetle Callosobruchus Maculates," Brazilian Journal of Medical and Biological Research, vol. 28(2), pp. 183-190 (1995).
Modgil R. Mehta, "Effect of Callosobruchus Chinensis (Bruchid) Infestation on Antinutritional Factors in Stored Legumes," Plant Foods Hum Nutr 50: 317-23 (1997).
Moraes et al., "Lima bean (*Phaseolus lunatus*) Seed Coat Phaseolin is Detrimental to the Cowpea Weevil (*Callosobruchus maculatus*)," Braz J Med Biol Res. 33: 191-198 (2000).
Osborn et al., "Insecticidal Activity And Lectin Homology of Arcelin Seed Protein," Science 240: 207-210 (1988).
Pusztai et al., "Nutritional Evaluation of the Tryspin (EC 3.4.21.4) Inhibitor From Cowpea (*Vigna unguiculata* Walp.)," The British Journal of Nutrition, vol. 68, No. 3, pp. 783-791 (1992).
Sugawara et al., "Insecticidal Peptide From Mungbean: A Resistant Factor Against Infestation with Azuki Bean Weevil," Journal of Agricultural and Food Chemistry, vol. 44, No. 10, pp. 3360-3364 (1996).
Suzuki et al., "cDNA Sequence and Deduced Primary Structure of an α-amylase Inhibitor from a Bruchid-Resistant Wild Common Bean," Biochemica Biophysica Acta, vol. 1206, No. 2, pp. 289-291 (1994).
Zhang et al., "Fabatins: New Antimicrobial Plant Peptides," FEMS Microbiology Letters, vol. 149, pp. 59-64 (1997).
Zhu et al., "An Insecticidal N-Acetylglucosamine-Specific Lectin Gene From Griffonia Simplicifolia," (*Leguminosae*). Plant Physiol 110: 195-202 (1996).
Zhu-Salzman et al., "Carbohydrate Binding and Resistance to Proteolysis Control Insecticidal Activity of Griffonia Simplicifolia Lectin II," Proc Natl Acad Sci U S A 95: 15123-15128 (1998).
Masao et al., "Biochemical and Genetic Basis of the Insect Resistance in Mungbean," Abstract Book of the 6th International Congress of Plant Molecular Biology (Jun. 2000).
Masayashi et al., Genomic Information of the Bruchid Resistance Locus, Br, In Mungbean, Abstract Book of the 6th International Congress of Plant Molecular Biology (Jun. 2000).

* cited by examiner

*Primary Examiner*—Medina A. Ibrahim
(74) *Attorney, Agent, or Firm*—Occhiuti Rohlicek & Tsao LLP

(57) ABSTRACT

The invention relates to transformed plant cells and plants having a novel nucleic acid and protein sequences from the mung bean *Vigna radiata*. The nucleic acid sequence, isolated from a bruchid resistant mung bean line, encodes a thionin-like protein with biocidal properties.

25 Claims, No Drawings

SEQUENCE LISTING

<160> NUMBER OF SEQ ID NOS: 10

<210> SEQ ID NO 1
<211> LENGTH: 299
<212> TYPE: DNA
<213> ORGANISM: Vigna radiata
<220> FEATURE:
<221> NAME/KEY: CDS
<222> LOCATION: (21)...(239)

<400> SEQUENCE: 1

```
acctcaacaa ttcatcactc atg gag aga aaa act ttc agc ttc ttg ttc tcg      53
                      Met Glu Arg Lys Thr Phe Ser Phe Leu Phe Ser
                       1               5                  10 ctc ctt ctc gtc tta gcc tct gat gtg gcc gta gag aga gga gag gct        101
Leu Leu Leu Val Leu Ala Ser Asp Val Ala Val Glu Arg Gly Glu Ala
                15                  20                  25 aga act tgt atg ata aag aaa gaa ggg tgg gga aaa tgc tta att gac        149
Arg Thr Cys Met Ile Lys Lys Glu Gly Trp Gly Lys Cys Leu Ile Asp
         30                  35                  40 acc acc tgt gca cat tcg tgc aag aac cgc ggt tac ata ggt gga gat        197
Thr Thr Cys Ala His Ser Cys Lys Asn Arg Gly Tyr Ile Gly Gly Asp
     45                  50                  55 tgc aaa ggc atg acg cgc acc tgt tat tgc ctc gtc aac tgt                239
Cys Lys Gly Met Thr Arg Thr Cys Tyr Cys Leu Val Asn Cys
 60                  65                  70 tgaaccttt tcgaatatca tatcatctta tcacaaataa atatagcagc atcactgcta      299
```

<210> SEQ ID NO 2
<211> LENGTH: 73
<212> TYPE: PRT
<213> ORGANISM: Vigna radiata

```
<400> SEQUENCE: 2

Met Glu Arg Lys Thr Phe Ser Phe Leu Phe Ser Leu Leu Val Leu
 1               5                  10                  15

Ala Ser Asp Val Ala Val Glu Arg Gly Glu Ala Arg Thr Cys Met Ile
            20                  25                  30

Lys Lys Glu Gly Trp Gly Lys Cys Leu Ile Asp Thr Thr Cys Ala His
        35                  40                  45

Ser Cys Lys Asn Arg Gly Tyr Ile Gly Gly Asp Cys Lys Gly Met Thr
 50                  55                  60

Arg Thr Cys Tyr Cys Leu Val Asn Cys
65                  70

<210> SEQ ID NO 3
<211> LENGTH: 156
<212> TYPE: DNA
<213> ORGANISM: Vigna radiata

<400> SEQUENCE: 3
gagagaggag aggctagaac ttgtatgata aagaaagaag ggtggggaaa atgcttaatt      60
gacaccacct gtgcacattc gtgcaagaac cgcggttaca taggtggaga ttgcaaaggc    120
atgacgcgca cctgctattg cctcgtcaac tgttga                              156

<210> SEQ ID NO 4
<211> LENGTH: 51
<212> TYPE: PRT
<213> ORGANISM: Vigna radiata

<400> SEQUENCE: 4

Glu Arg Gly Glu Ala Arg Thr Cys Met Ile Lys Lys Glu Gly Trp Gly
 1               5                  10                  15

Lys Cys Leu Ile Asp Thr Thr Cys Ala His Ser Cys Lys Asn Arg Gly
            20                  25                  30

Tyr Ile Gly Gly Asp Cys Lys Gly Met Thr Arg Thr Cys Tyr Cys Leu
        35                  40                  45

Val Asn Cys
    50

<210> SEQ ID NO 5
<211> LENGTH: 299
<212> TYPE: DNA
<213> ORGANISM: Artificial Sequence
<220> FEATURE:
<223> OTHER INFORMATION: Synthetically generated oligonucleotide
<220> FEATURE:
<221> NAME/KEY: CDS
<222> LOCATION: (21)...(239)

<400> SEQUENCE: 5
acctcaacaa ttcatcactc atg gag aga aaa act ttc agc ttc ttg ttc ttg     53
                     Met Glu Arg Lys Thr Phe Ser Phe Leu Phe Leu
                      1               5                  10 ctc ctt ctt gtc tta gcc tct gat gtg gcc gta gag aga gga gag gct      101
Leu Leu Leu Val Leu Ala Ser Asp Val Ala Val Glu Arg Gly Glu Ala
             15                  20                  25 aga act tgt atg ata aag aaa gaa ggg tgg gga aaa tgc tta att gac      149
Arg Thr Cys Met Ile Lys Lys Glu Gly Trp Gly Lys Cys Leu Ile Asp
         30                  35                  40 acc acc tgt gca cat tcg tgc aag aac cgc ggt tac ata ggt gga aat     197
Thr Thr Cys Ala His Ser Cys Lys Asn Arg Gly Tyr Ile Gly Gly Asn
```

```
              45                  50                  55
tgc aaa ggc atg acg cgc acc tgc tat tgc ctc gtc aac tgt        239
Cys Lys Gly Met Thr Arg Thr Cys Tyr Cys Leu Val Asn Cys
 60                  65                  70 tgaacccttt tcgaatatca tatcatctta tcacaaataa atatagcagc atcactgcta    299
```

<210> SEQ ID NO 6
<211> LENGTH: 73
<212> TYPE: PRT
<213> ORGANISM: Artificial Sequence
<220> FEATURE:
<223> OTHER INFORMATION: Synthetically generated peptide

<400> SEQUENCE: 6

```
Met Glu Arg Lys Thr Phe Ser Phe Leu Phe Leu Leu Leu Val Leu
 1               5                  10                  15

Ala Ser Asp Val Ala Val Glu Arg Gly Glu Ala Arg Thr Cys Met Ile
                20                  25                  30

Lys Lys Glu Gly Trp Gly Lys Cys Leu Ile Asp Thr Thr Cys Ala His
            35                  40                  45

Ser Cys Lys Asn Arg Gly Tyr Ile Gly Gly Asn Cys Lys Gly Met Thr
    50                  55                  60

Arg Thr Cys Tyr Cys Leu Val Asn Cys
 65                  70
```

<210> SEQ ID NO 7
<211> LENGTH: 141
<212> TYPE: DNA
<213> ORGANISM: Artificial Sequence
<220> FEATURE:
<223> OTHER INFORMATION: Synthetically generated oligonucleotide

<400> SEQUENCE: 7

```
agaacttgta tgataaagaa agaagggtgg ggaaaatgct taattgacac cacctgtgca    60
cattcgtgca agaaccgcgg ttacataggt ggaaattgca aaggcatgac gcgcacctgc   120
tattgcctcg tcaactgttg a                                              141
```

<210> SEQ ID NO 8
<211> LENGTH: 46
<212> TYPE: PRT
<213> ORGANISM: Artificial Sequence
<220> FEATURE:
<223> OTHER INFORMATION: Synthetically generated peptide

<400> SEQUENCE: 8

```
Arg Thr Cys Met Ile Lys Lys Glu Gly Trp Gly Lys Cys Leu Ile Asp
 1               5                  10                  15

Thr Thr Cys Ala His Ser Cys Lys Asn Arg Gly Tyr Ile Gly Gly Asn
                20                  25                  30

Cys Lys Gly Met Thr Arg Thr Cys Tyr Cys Leu Val Asn Cys
            35                  40                  45
```

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9

```
cccgggacct caacaattca tcactcatg                                       29
```

```
<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
cgagctctca acagttgacg aggcaat                                     27
```

TRANSGENIC PLANTS EXPRESSING BIOCIDAL PROTEINS AND METHOD OF PRODUCING THE SAME

RELATED TECHNICAL FIELD

This application is a continuation-in-part of and claims priority to U.S. application Ser. No. 10/409,818, filed Apr. 8, 2003 now U.S. Pat. No. 7,091,312, which is a divisional application and claims priority to U.S. application Ser. No. 09/686,332, filed Oct. 11, 2000, now U.S. Pat. No. 6,653,463, the contents of which are incorporated herein by reference.

BACKGROUND

Advances in biotechnology have enabled the generation of plants that express recombinant proteins. Plants can be engineered to produce a variety of polypeptides with desirable qualities. Such polypeptides include enzymes that produce secondary metabolites, proteins with medicinal or pharmaceutical properties, and proteins that endow the plants with new traits (e.g., resistance to diseases and environmental conditions).

Given the vulnerability of agricultural crops to damage by insects, other pests, and pathogens, there is a need to provide additional protective means and agents. Traditional breeding techniques have identified plant lines with Mendelian traits endowing resistance to pests and pathogens. Modem molecular biology techniques can now be applied to isolate the critical nucleic acids and proteins with these traits in order to enhance the resistance of plants to pests and pathogens.

SUMMARY

The invention relates to a novel mung bean nucleic acid that is expressed in a mung bean plant line resistant to insect attack, but not expressed in sensitive plant lines. The nucleic acid encodes a polypeptide that possesses an insecticidal activity and is similar to thionin proteins. Shown below is the sequence of the mung bean thionin nucleic acid (SEQ ID NO: 1), designated as *Vigna radiata* Cysteine-Rich Protein (VrCRP):

```
                                          SEQ ID NO: 1
ACCTCAACAATTCATCACTCATGGAGAGAAAAACTTTCAGCTTCTTGTTC

TIGCTCCTTCTCGTCTTAGCCTCTGATGTGGCCGTAGAGAGAGGAGAGGC

TAGAACTTGTATGATAAAGAAAGAAGGGTGGGAAAATGCTTAATTGACA

CCACCTGTGCACATTCGTGCAAGAACCGCGGTTACATAGGTGGAGATTGC

AAAGGCATGACGCGCACCTGCTATTGCCTCGTCAACTGTTGAACCCTTTT

CGAATATCATATCATCTTATCACAAATAAATATAGCAGCATCACTGCTA
```

The initiator and terminator codons are underlined and in boldface. Shown below is the sequence of the mung bean thionin polypeptide sequence (SEQ ID NO: 2), designated as "VrCRP":

```
                                          SEQ ID NO: 2
MERKTFSFLFSLLLVLASDVAVERGEARTCMIKKEGWGKCLIDTTCAHSC

KNRGYIGGDCKGMTRTCYCLVNC.
```

The invention is also based on the discovery that a polypeptide derived from VrCRP, which has the VrCRP signal sequence removed, is biologically active as an insecticide and fungicide. Shown below is a nucleic acid (SEQ ID NO: 3) that encodes this polypeptide (SEQ ID NO: 4):

```
                                          SEQ ID NO: 3
GAGAGAGGAGAGGCTAGAACTTGTATGATAAAGAAAGAAGGGTGGGGAAA

ATGCTTAATTGACACCACCTGTGCACATTCGTGCAAGAACCGCGGTTACA

TAGGTGGAGATTGCAAAGGCATGACGCGCACCTGCTATTGCCTCGTCAAC

TGT TGA.
```

```
                                          SEQ ID NO: 4
ERGEARTCMIKKEGWGKCLIDTTCAHSCKNRGYIGGDCKGMTRTCYCLV

NC.
```

It was unexpected that this polypeptide, once expressed in a non-mung bean plant cell or plant, retains the activities.

Accordingly, in one aspect, the invention features a transformed or transgenic plant cell having a recombinant nucleic acid encoding a heterologous polypeptide that contains an amino acid sequence at least 60% (i.e., any number between 60% and 100%, inclusive) identical to SEQ ID NO: 4. The polypeptide has insecticidal, fungicidal, or bactericidal activity. Examples of the polypeptide include SEQ ID NOs: 2 and 4 mentioned above and SEQ ID NOs: 6 and 8 described in Example 1 below. The plant cell can be a dicot plant cell (e.g., a tobacco cell) and a monocot plant cell (e.g., a rice cell). The transformed plant cell can be made by introducing into a plant cell a recombinant nucleic acid that encodes the heterologous polypeptide and expressing the polypeptide in the cell.

In another aspect, the invention features a transgenic plant whose genome has a recombinant nucleic acid encoding the just-described heterologous polypeptide. Examples of the transgenic plant include a dicot plant (e.g., a tobacco) and a monocot plant (e.g., a rice). In one embodiment, the plant is resistant to an insect, e.g., *Spodoptera litura, Callosobruchus chinensis*, or *Callosobruchus maculatus* (F.) In another embodiment, the plant is resistant to a fungus, such as *Fusurium oxysporum* or *F. oxysporum* f. sp. *pisi*. In yet another embodiment, the plant is resistant to a bacterium, e.g., *Xanthomonas campestris* pv. *Vesicatoria, Staphylococcus epidermidis*, or *Salmonella typhimurium*. The transgenic plant can be made by introducing into a plant cell a recombinant nucleic acid that encodes the heterologous polypeptide, expressing the polypeptide, and cultivating the cell to generate a plant.

A "heterologous" polypeptide or nucleic acid is one that originates from a foreign species, or, if from the same species, is substantially modified from its original form. For example, a heterologous promoter can be operably linked to a coding nucleic acid sequence of a plant. If a promoter and its down stream coding sequence are from the same species, one or both of them have been substantially modified from their original forms.

A "percent identity" of two amino acid sequences or of two nucleic acids is determined using the algorithm of Karlin and Altschul (1990) *Proc. Natl. Acad. Sci.* USA 87:2264-68, modified as in Karlin and Altschul (1993) *Proc. Natl. Acad. Sci.* USA 90:5873-77. Such an algorithm is incorporated into the NBLAST and XBLAST programs (version 2.0) of Altschul, et al. (1990) *J Mol. Biol.* 215:403-10. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. Where gaps exist between two sequences, Gapped BLAST can be utilized as described in Altschul et al. (1997) *Nucleic Acids Res.* 25(17):3389-3402. When utilizing BLAST and Gapped BLAST programs, the default parameters of the respective programs (e.g., XBLAST and NBLAST) can be used.

A transgene is to a nucleic acid sequence (encoding, e.g., one or more subject thionin polypeptides), which is partly or entirely heterologous to a plant cell into which it is introduced, or, is homologous to an endogenous gene of the plant or cell into which it is introduced but is intended to be inserted into the plant genome in such a way as to alter the genome (e.g., it is inserted at a location which differs from that of the natural gene or its insertion results in a knockout). A transgene can include one or more operably linked transcriptional regulatory sequences (e.g., an enhancer sequence) and any other nucleic acid, such as an intron, that may be necessary for optimal expression of a nucleic acid of interest. A transgenic cell is to a cell containing a transgene. A transgenic plant is any plant in which one or more, or all, of the cells of the plant include a transgene. The transgene can be introduced into the cell by introduction into a precursor cell by way of deliberate genetic manipulation, such as by T-DNA mediated transfer, electroporation, or protoplast transformation. The transgene may be integrated within a chromosome, or it may be an extrachromosomally replicating DNA.

The details of one or more embodiments of the invention are set forth in the accompanying and the description below. Other features, objects, and advantages of the invention will be apparent from the description and drawings, and from the claims.

DETAILED DESCRIPTION

This invention is based, at least in part, on an unexpected discovery that expression of a mung bean biocidal protein or its functional equivalent in a non-mung bean plant increases the ability of the plant to resist insects, fungus, or bacteria.

Accordingly, the invention features a transformed plant cell containing a heterologous recombinant nucleic acid that encodes a polypeptide that includes a sequence at least 60% identical to SEQ ID NO: 4, or its functional equivalent. The plant cell can be a dicot plant cell or a monocot plant cell, such as a cell of maize, wheat, rice, soybean, tomato, tobacco, peanut, potato, mango, bean, carrots, cucumber, pepper, sugar beets, sunflower, yam, arabidopsis, rape seed, sunflower, or petunia.

A functional equivalent of SEQ ID NO: 4 refers to a polypeptide derived from SEQ ID NO: 4, e.g., a fusion polypeptide or a polypeptide having one or more point mutations, insertions, deletions, truncations, or combination thereof. In particular, functional equivalents of SEQ ID NO: 4 include polypeptides, whose sequences differ from SEQ ID NO: 4 by one or more conservative amino acid substitutions or by one or more non-conservative amino acid substitutions, deletions, or insertions as described in U.S. Pat. No. 6,653,463. Such a functional equivalent can be encoded by a nucleic acid that hybridizes under high stringency conditions to a probe the sequence of which consists of SEQ ID NO: 1 or 3. The term "hybridizes under stringent conditions" refers to conditions for hybridization in 6× sodium chloride/sodium citrate (SSC) at about 45° C., followed by one or more washes in 0.2×SSC, 0.1% SDS at 50-65° C.

All of the above-described functional equivalents retain substantially at least one of the activities of SEQ ID NO: 4, e.g., the insecticidal activity, fungicidal activity, anti-bacterium activity, or mRNA translation inhibition activity, as described in U.S. Pat. No. 6,653,463. These activities can be determined by the assays described therein or in the examples presented below. Other methods for determining the activities are well-known in the art.

A transformed plant cell of the invention can be produced by introducing into a plant cell a recombinant nucleic acid that encodes the heterologous polypeptide described herein and expressing the polypeptide in the cell. Techniques for transforming a wide variety of plant cells are well known in the art and described in the technical and scientific literature. See, for example, Weising et al. (1988) *Ann. Rev. Genet.* 22:421-477. To express a heterologous gene in a plant cell, the gene can be combined with transcriptional and translational initiation regulatory sequences that will direct the transcription of the gene and translation of the encoded protein in the plant cell. For example, for overexpression, a constitutive plant promoter may be employed. A "constitutive" promoter is active under most environmental conditions and states of cell differentiation. Examples of constitutive promoters include the cauliflower mosaic virus (CaMV) 35S transcription initiation region, the 1'- or 2'-promoter derived from T-DNA of *Agrobacterium tumafaciens*, the ACT11 and Cat3 promoters from *Arabidopsis* (Huang et al. (1996) *Plant Mol. Biol.* 33:125-139 and Zhong et al. (1996) *Mol. Gen. Genet.* 251:196-203), the stearoyl-acyl carrier protein desaturase gene promoter from *Brassica napus* (Solocombe et al. (1994) *Plant Physiol.* 104:1167-1176), the GPc1 and Gpc2 promoters from maize (Martinez et al. (1989) *J. Mol. Biol.* 208:551-565 and Manjunath et al. (1997) *Plant Mol. Biol.* 33:97-112).

Alternatively, a plant promoter may be employed to direct expression of the polypeptide described therein in a specific cell type (i.e., tissue-specific promoters) or under more precise environmental or developmental control (i.e., inducible promoters). A "tissue-specific promoter" refers to a DNA sequence that serves as a promoter, i.e., regulates expression of a selected DNA sequence operably linked to the promoter, and which effects expression of the selected DNA sequence in specific cells of a tissue, such as a leaf, a root, or a stem. Examples of tissue-specific promoters include the root-specific ANR1 promoter (Zhang and Forde (1998) *Science* 279:407) and the photosynthetic organ-specific RBCS promoter (Khoudi et al. (1997) *Gene* 197: 343).

Examples of environmental conditions that may affect transcription by inducible promoters include anaerobic conditions, elevated temperature, the presence of light, spray with chemicals or hormones, or infection of a pathogen. Promoters are known which respond to excessive heat, tissue injury, pathogen infection, or cell wounding, e.g., wounding due to pest attack. Known signals for promoters included methyl jasmonate, absiscic acid, gibberillins, salicylic acid, ethylene, $HgCl_2$, and $H_2O_2$. Methyl jasmonate responsive promoters include vspB (Mason et al. (1993) *Plant Cell* 5:241-251), and the tomato HMG2 promoter (U.S. Pat. No. 5,689,056). An example of a gibberillin response promoter is the Amy1/6-4 promoter of rice (Skriver et al. (1991) *Proc. Natl. Acad. Sci. USA* 88:7266-7270). Promoters that respond to pathogen infection include the grape stilbene synthase promoter (U.S. Pat. No. 6,072,103).

Promoters that respond to cell wounding include the win1 and win2 promoters (Weiss and Bevan (1991) *Plant Physiol.* 96:943-951), and the PinII promoter (U.S. Pat. No. 5,684, 239). Any of these promoters can be operably linked to a nucleic acid sequence of SEQ ID NO: 1 or 3 in order to regulate expression of the polypeptide of SEQ ID NO: 2 or 4. Similarly, any of these promoters can be operably linked to variants or fragments of SEQ ID NO: 1, or other similar coding nucleic acid sequences.

For proper polypeptide expression, a polyadenylation region at the 3'-end of the coding region should be included. The polyadenylation region can be derived from the natural gene, from a variety of other plant genes, or from T-DNA.

A marker gene can also be included to confer a selectable phenotype on plant cells. For example, the marker gene may encode a protein that confers biocide resistance, antibiotic resistance (e.g., resistance to kanamycin, G418, bleomycin, hygromycin), or herbicide resistance (e.g., resistance to chlorosulfuron or Basta).

A recombinant nucleic acid that encodes a heterologous polypeptide described herein may be introduced into the genome of a desired plant host cell by a variety of conventional techniques. For example, the recombinant nucleic acid may be combined with suitable T-DNA flanking regions and introduced into a conventional *Agrobacterium tumefaciens* host vector. The virulence functions of the *Agrobacterium tumefaciens* host will direct the insertion of the recombinant nucleic acid and adjacent marker into the plant cell DNA when the cell is infected by the bacteria. *Agrobacterium tumefaciens*-mediated transformation techniques, including disarming and use of binary vectors, are well described in the scientific literature. See, e.g., Horsch et al. (1984) *Science* 233:496-498, Fraley et al. (1983) *Proc. Natl. Acad. Sci. USA* 80:4803, and Gene Transfer to Plants, Potrykus, ed., Springer-Verlag, Berlin, 1995.

One implementation of the current invention utilizes *Agrobacterium* to introduce the desired construct into plant cells in a manner described in U.S. Pat. Nos. 5,177,010, 5,104,310, 5,149,645, 5,469,976, 5,464,763, 4,940,838, 4,693,976, 5,591,616, 5,231,019, 5,463,174, 4,762,785, 5,004,863, and 5,159,135; and European Patent Applications 116718, 290799, 320500, 604662, 627752, 0267159, and 0292435). The method can be used with both dicotyledonous plants cells (Bevan et al. (1982) *Ann. Rev. Genet.* 16:357-384; Rogers et al. (1986) *Methods Enzymol.* 118: 627-641), and monocotyledonous plant cells. (Hernalsteen et al. (1984) *EMBO J* 3:3039-3041; Hooykass-Van Slogteren et al. (1984) *Nature* 311:763-764; Grimsley et al. (1987) *Nature* 325:1677-179; Boulton et al. (1989) *Plant Mol. Biol.* 12:31-40; Gould et al. (1991) *Plant Physiol.* 95:426-434). The method employs binary *Agrobacterium* T-DNA vectors (Hoekema et al. (1983) *Nature* 03:179; Bevan (1984) *Nuc. Acid Res.* 12:8711-8721), and the co-cultivation procedure (Horsch et al. (1985) *Science* 227: 1229-1231).

Additional steps may be required to prepare a desired nucleic acid sequence for plant transformation. For example, in order to utilize T-DNA mediated transformation, a coding sequence, operably linked to a heterologous promoter, is ligated into a binary vector, between the left and right border sequences of T-DNA. The binary vector further includes an Hph gene coding for hygromycin resistance. The binary vector containing the desired construction is transformed into an *E. coli* strain, e.g., DH5α. Subsequently, the binary plasmid is transferred into an *Agrobacterium*, e.g., *Agrobacterium* strain LBA4404, using a tri-parental mating.

Meanwhile, plants are prepared to receive the T-DNA with the transgene. For example, leaf discs are obtained from axenically grown tobacco seedlings. The discs are incubated for 8 hours on sterile filter papers overlaid on tobacco nurses cells on a feeder plate containing modified MS medium with Nitsch vitamins, 100 ml/L myo-inositol, 30 mg/L sucrose, 0.4 mg/L BAP, 1 mg/L 2,4-D (dichlorophenoxyacetic acid), 8 g/L agar. To establish co-cultivation, the filters bearing the leaf disks are submersed in a suspension of the *Agrobacterium* bearing the desired binary vector, the bacteria being a concentration of approximately $1 \cdot 10^9$ cell/ml, and vacuum infiltrated (3×1 minute). The filters and leaf discs are incubated on the nurse plate for 48 hours at 25° C. with indirect light. Then the discs are transferred to selection/regeneration plates containing MS salts, Nitsch vitamins, 100 ml/L myo-inositol, 20 g/L sucrose, 2 mg/L zeatin, 4 g/L agar, 500 μg/ml carbemicillin and an appropriate antibiotic to select for, e.g., the hygromycin resistance gene. The plates are placed in a growth chamber at 25° C. for 18 hours with light. The resulting shoots were transferred to rooting media, grown into plantlets, transferred to soil, and grown into plants in a green house. One skilled in the art can adapt this method to transform other species of plants.

Other methods for transforming plant cells are available. Of particular utility for transforming monocotyledonous plants or plant cells are methods of protoplast transformation which include, but are not limited to, protoplast transformation through calcium-, polyethylene glycol (PEG)- or electroporation-mediated uptake of naked DNA (see Paszkowski et al. (1984) *EMBO J* 3:2717-2722, Potrykus et al. (1985) *Molec. Gen. Genet.* 199:169-177; Fromm et al. (1985) Proc. Nat. Acad. Sci. USA 82:5824-5828; Shimamoto (1989) *Nature* 338:274-276), microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; Gordon-Kamm et al., 1990, *Plant Cell* 2:603-618), whiskers technology (see U.S. Pat. Nos. 5,302,523 and 5,464,765), and viral vector systems (see, U.S. Pat. Nos. 5,316,931, 5,589, 367, 5,811,653, and 5,866,785).

Transformed plant cells which are obtained by any of the above transformation techniques can be cultured to regenerate a whole plant. Such regeneration techniques rely on manipulation of certain phytohormones in a tissue culture growth medium, typically relying on a biocide or herbicide marker that has been introduced together with the heterologous gene. Plant regeneration from cultured protoplasts is described in Evans et al., Protoplasts Isolation and Culture, Handbook of Plant Cell Culture, pp. 124-176, MacMillilan Publishing Company, New York (1983); and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. (1987) *Ann. Rev. Plant Phys.* 38:467-486. Once the heterologous gene has been confirmed to be stably incorporated in the genome of a transgenic plant, it can be introduced into other plants by sexual crossing. Any of a number of standard breeding techniques can be used, depending upon the species to be crossed.

A transformed plant or transformed plant tissue can be assayed for resistance to pathogens, insects, and other pests (e.g., by a field trial or by a method described herein). The presence and copy number of a heterologous gene in a transgenic plant can be determined using methods well known in the art, e.g., Southern blotting analysis. Expression of the heterologous polypeptide in a transgenic plant may be confirmed by detecting the corresponding mRNA or protein in the transgenic plant. Means for detecting and quantifying mRNA or proteins are well known in the art.

Without further elaboration, it is believed that the above description has adequately enabled the present invention. The following examples are, therefore to be construed as merely illustrative, and not limitative of the remainder of the disclosure in any way whatsoever. All of the publications cited herein are hereby incorporated by reference in their entirety.

EXAMPLE 1

In this example, transgenic tobacco plants containing mung bean defensin VrD1 were generated and analyzed for their resistance against the common cutworm *S. litura*.

A cDNA encoding mung bean defensin VrCRP was isolated from a bruchid resistant isogenic line of mung bean *V. radiata* VC6089A ("VC6089A") by suppressive subtractive hybridization (Chen et al., 2002, Bot. Bull. Acad. Sin. 43:251-259; and Chen et al., 2002, J. Agric. Food Chem. 50:7258-7263). VrD1 genomic DNA was cloned by polymerase chain reaction (PCR) amplification using total cellular DNA of VC6089A as a template and a pair of oligonucleotide primers designed based on 5' and 3' nucleotide sequences of VrD1. A 402 bp DNA fragment was obtained and cloned into a pGEM-T easy vector and sequenced. Comparison of this nucleotide sequence with that of VrD1cDNA revealed a single 103 bp intron located between serine 18 and aspartic acid 19 of the 27 amino acid signal peptide of VrD1. To clone VrD1 cDNA, the 103 bp intron was eliminated by inverse PCR using the VrD1 genomic DNA in pGEM-T easy vector as a template. An antisense primer complimentary to the last 30 bp of the 3'-end of exon 1 in VrD1 genomic DNA and a sense primer corresponding to first 30 bp of the 5'-end of exon 2 were used for inverse PCR. The PCR product was circularized by T4 ligase, and the VrD1 cDNA insert in the pGEM-T easy vector ("VrD1/pGEM-T easy vector") was verified by colony PCR and nucleotide sequencing (Chen et al., 2004, J. Agric. Food Chem. 52:2256-2261.).

It was found that this cDNA encodes the following polypeptide: MERKTFSFLFLLLLVLASDVAVERGEARTCMIKKEGWGKCLIDTTCAHSCKNRG YIGG NCKGMTRTCYCLVNC (SEQ ID NO: 6). The polypeptide differs from SEQ ID NO: 2 by one residue (underlined). The signal sequence-free version is RTCMIKKEGWGKCLIDTTCAHSCKNRGYIGGNCKGMTRTCYCLVNC (SEQ ID NO: 8). Listed below are the nucleotide sequences encoding SEQ ID NOs:6 and 8, i.e., SEQ ID NOs: 5 and 7, respectively:

SEQ ID NO: 5
ACCTCAACAATTCATCACTC<u>ATG</u>GAGAGAAAAACTTTCAGCTTCTTGTTC

TTGCTCCTTCTTGTCTTAGCCTCTGATGTGGCCGTAGAGAGAGGAGAGGC

TAGAACTTGTATGATAAAGAAAGAAGGGTGGGAAAATGCTTAATTGACA

CCACCTGTGCACATTCGTGCAAGAACCGCGGTTACATAGGTGGA<u>AAT</u>TGC

AAAGGCATGACGCGCACCTGCTATTGCCTCGTCAACTGT<u>TGA</u>ACCCTTTT

CGAATATCATATCATCTTATCACAAATAAATATAGCAGCATCACTGCTA

SEQ ID NO: 7
AGAACTTGTATGATAAAGAAAGAAGGGTGGGAAAATGCTTAATTGACAC

CACCTGTGCACATTCGTGCAAGAACCGCGGTTACATAGGTGGA<u>AAT</u>TGCA

AAGGCATGACGCGCACCTGCTATTGCCTCGTCAACTGT TGA.

To construct an expression vector, a 255-bp fragment encoding the full length VrD1cDNA was amplified by PCR using the just described VrD1/pGEM-T easy vector as a template and a sense primer 5'-CCCGGGACCTCAACAATTCATCACTCATG-3' (SEQ ID NO:9) containng with a Sma I site and an antisense primer 5'-CGAGCTCTCAACAGTTGACGAGGCAAT-3' (SEQ ID NO:10) containing a Sac I site. The PCR amplified fragment was digested with Sma I and Sac I enzymes and ligated into Sma I/Sac I digested pBI121 between the CaMV 35S promoter and the Nos terminator. The resultant plant expression vector was named VrD1/pBI121.

To investigate whether VrD1 plays a role in protecting plant from insect pests and fungal pathogens, the just-described VrD1/pBI121 vector was introduced into *Agrobacterium tumefaciens* strain LBA4404 by the freeze-thaw method described in An et al. (1988) Binary vector, In: Gelvin, S. B., Schilperoort, R. A., Verma, D. P. S. (eds) Plant Molecular Biology Manual. Kluwer Academic Publishers, Dordrecht ppA3:1-19.

Leaf discs of tobacco (*Nicotiana tabacum* cv. Wisconsin 38) were transformed via *A. tumefacience* by the co-cultivation method described in Horsch et al. (1985) Science 227:1229-1233. Regenerated tobacco plants were selected in a medium containing kanamycin (100 mg/L). The selected transformants were further confirmed by colony PCR. Shoots of the transgenic tobacco were then rooted on an MS medium containing 50 mg $l^{-1}$ kanamycin. The rooted plantlets were transferred to soil and grown in a greenhouse. The primary transformants were designated T0 generation plants. Six transgenic tobacco lines, L1~L6, were obtained.

To verify mRNA expression of VrD1 in the T0 generation transgenic plants, total RNA was extracted from the 6 transgenic tobacco lines by RNeasy plant mini kit (Qiagen) and then subjected to northern blot analysis. Twenty five micrograms of total RNA was fractionated in 1% agarose gels by electrophoresis, transferred onto an Immobilon-NY$^+$ charged nylon membrane, and hybridized with digoxigenin (DIG)-labeled probes containing the VrD1 coding sequence. The labeling, hybridization, and washing procedure were performed according to the manual in a DIG Northern starter Kit (Roche). It was found that a VrD1 transcript was detected in L1, L2, L3 and L6, but not in L4 and L5.

Proteins were extracted from 100 g of leaves of the T0 generation transgenic tobacco and chromatographed on a CM-Sepharose column (2.6 cm×30 cm) by standard techniques. Two major protein peaks and 6 minor peaks were eluted from the column. Each of the 6 minor peak fractions was pooled and concentrated. One hundred mircoliters of each concentrated protein sample was separated on NuPAGE 4%~12% Bis-Tris gel (Invitrogen) ("gradient PAGE") and stained with Coomassie Brilliant Blue. The results showed that a protein band with molecular weight corresponding to that of VrD1, MW. 5,114, was detected in peak 6. Fractions of peak 6 were then pooled, concentrated, and chromatographed on a Superdex Peptide HR 10/30 gel filtration column (1 cm×30 cm). A protein peak containing recombinant VrD1 (rVrD1) was further subjected to gradient PAGE, and rVrD1 was visualized by Coomassie Brilliant Blue staining and western blotting using antiVrD1 antiserum. Purified rVrD1 on a gradient PAGE gel was also transferred to a 0.45 μm Immobilon-P PVDF membrane and the N-terminal amino acid sequence of the rVrD1 was determined. Twenty-two N-terminal amino acids thus determined matched the N-terminal amino acid sequence deduced from VrD1 cDNA. The results indicated that the full-length VrD1 cDNA was expressed in the transgenic tobacco and that the expressed rVrD1 precursor was properly processed to form the mature rVrD1.

To examine the insect-resistance of the 6 transgenic tobacco plants, 3rd instar larvae of *Spodoptera litura* were reared on leaves from transgenic tobaccos, non-transgenic tobaccos ("NT"), and control tobaccos (tobaccos transformed with the control pBI121 expression vector ("C"), respectively. The leaves were kept wet by sponge and changed every 2-3 days. At day 7, the survival ratio of the larvae, weight of the leaves, area of the leaves and average weight of the insects were measured. The results are summarized in Table 1 below:

TABLE 1

Statistical analysis of transgenic tobacco bioassay.

| Tobacco plants | No. of larvae | Average weight of leave consumed (g) | Average area of leave consumed ($cm^2$) | Average weight of larva (g) | Survival rate of larva (%) |
|---|---|---|---|---|---|
| NT | 7 | $1.018 \pm 0.106^A$ | $30.137 \pm 6.145^A$ | $0.291 \pm 0.067^A$ | 100 |
| C | 8 | $1.049 \pm 0.066^A$ | $15.219 \pm 2.104^B$ | $0.165 \pm 0.025^B$ | 100 |
| L1 | 6 | $0.405 \pm 0.046^B$ | $3.348 \pm 0.752^C$ | $0.051 \pm 0.009^C$ | 100 |
| L2 | 5 | $0.502 \pm 0.057^B$ | $2.838 \pm 0.506^C$ | $0.045 \pm 0.004^C$ | 100 |
| L3 | 6 | $0.363 \pm 0.003^B$ | $3.673 \pm 0.342^C$ | $0.056 \pm 0.005^C$ | 100 |
| L4 | 6 | $0.463 \pm 0.056^B$ | $3.863 \pm 1.201^C$ | $0.065 \pm 0.013^C$ | 100 |
| L5 | 6 | $0.525 \pm 0.022^B$ | $6.613 \pm 1.577^C$ | $0.074 \pm 0.016^C$ | 100 |
| L6 | 6 | $0.463 \pm 0.030^B$ | $4.235 \pm 0.265^C$ | $0.060 \pm 0.004^C$ | 100 |

Note:
The mean values are significantly different at P = 1% among the groups denoted by different letters The results indicated that all larvae reared on leaves from the 6 transgenic tobacco consumed much less amounts of leave than those reared on leaves of the control plant or the non-transgenic tobacco. The larvae reared on the transgenic tobacco leaves gained much less weights than those fed on leaves of the control or non-transgenic tobacco. Furthermore, the sizes of the larvae reared on leaves from the transgenic tobacco were also much smaller than those of the larvae on control or non-transgenic tobacco. The results suggest that VrD 1 plays a defensive role against insect pests in transgenic tobacco plants and that VrD1 gene is useful for engineering economically important crops.

EXAMPLE 2

In this example, transgenic rice plants expressing VrD1 were generated. The above-described VrD1 cDNA was inserted into a pMTC510 expression vector, which included a promoter of RP5, a rice prolamin gene. It is known that the RP5 promoter drives a high level expression of a gene, e.g., a GUS reporter gene, exclusively in rice endosperm cells; that transgenic rice lines could transmit the RP5/GUS chimeric gene to R2 seeds without gene silencing; and that their expression remained at levels similar to that in primary transformants (Su et al., 2001, J. Plant Physiol. 158:247-254.). The resultant plant expression vector, VrD1/pMTC510, was transformed into *E. coli* TOP 10'F. Transformed *E. coli* was screened on an ampicillin-containing LB plate. The VrD1/pMTC510 vector was purified from the screend *E. coli* and subjected to DNA sequence analysis to ensure the VrD1 cDNA fragment in the correct reading frame. The vector was then introduced into *Agrobacterium tumefaciens* strain LBA4404 by a freeze-thaw method (An et al. (1988) Binary vector, In: Gelvin, S. B., Schilperoort, R. A., Verma, D. P. S. (eds) Plant Molecular Biology Manual. Kluwer Academic Publishers, Dordrecht ppA3:1-19.). Transformed *A. tumefaciens* LBA4404 clones were confirmed by colony PCR.

To generate transformed rice cells, scutellum-derived calli from mature seeds of the rice cultivar Tainung 67 were infected with the above-mentioned transformed *A. tumefacience* LBA4404 in the manner described in Toki (1997) Plant Mol. Biol. Rep. 15:16-21. Regenerated rice plants were selected in a medium containing hygromycin (100 mg/L). A total of seventy transgenic rice lines were obtained. To confirm VrD1 expression, seeds from the transgenic rice plants were used to isolate VrD1 protein.

More specifically, one hundred grams of dry seeds harvested from the primary transgenic rice lines were ground in a mill. The seed powder was extracted in 500 ml of an extraction buffer (10 mM $NaH_2PO_4$, 15 mM $Na_2HPO_4$, 500 mM NaCl, 100 mM KCl, 2 mM EDTA, 1.5% polyvinylpolypyrrolidine and 1 mM phenylmethylsulfluoride, pH 6.4) at 4° C. for 16 hours under continuous stirring. Solid materials were subsequently removed by centrifugation at 11,000×g for 30 minutes. Solid ammonium sulfate was then added to the supernatant to obtain 30-80% saturated ammonium sulfate fraction (30-80% AS fraction). The 30-80% AS fraction was dissolved in distilled water and dialyzed against 20 mM Tris-HCl, pH 7.0 (buffer A). The dialyzed solution was passed through a CM-Sepharose CL-6B (Pharmacia) column (2.6 cm×30 cm) previously equilibrated with buffer A. The column was washed with 10 volume of buffer A and eluted with a linear gradient (800 ml total volume) of 0-0.5 M NaCl in buffer A. Fractions (12 ml each) were collected at a flow rate of 4 ml/minute. Proteins in the fractions were monitored at 280 nm. Aliquots of protein fractions were analyzed on NuPAGE 4-12% Bis-Tris gel (Invitrogen). Fractions having a protein band of about 5.1 kDa were pooled, and concentrated with a MasterFlex ultrafiltration apparatus (Millipore). The concentrated solution was further purified by FPLC on a Superdex Peptide HR 10/30 column (Pharmacia) and eluted with buffer A containing 150 mM NaCl at a flow rate of 0.5 ml/minute. The protein concentration was determined by a modified Lowry method (Alam, 1992, Anal. Biochem. 203:121-126). Protein peaks eluted from the gel filtration column was analyzed by gradient PAGE. Analysis of six protein peaks with the gradient PAGE indicated that Peak 3 contained VrD1. It was found that Peak 3 contained another unknown protein ran very closely to VrD1. Protein on the gel was transferred to a 0.45 µm Immobilon-P PVDF membrane (Millipore) and subjected to N-terminal amino acid sequencing. The results indicate that VrD1 cDNA was expressed in seeds of transgenic rice plants. These transgenic rice seeds can be used to analyze the resistance against rice bruchid.

EXAMPLE 3

Assays for examining antimicrobial activity of VrD1 were carried out in the manner described in Terras et al., (1992) J. Biol. Chem. 267: 15301-15309; and Broekaert et al., (1990) FEMS microbial. Lett. 9: 55-60). More specifically, a VrD1 solution was sterilized by passing through a 0.22 um filter. The VrD1 solution was diluted to different concentrations: 1, 5, 10, 50, 100, 200 and 1000 µg/ml. Twenty micorliters of each diluted solution were mixed with 80 µl of fungal spore or mycelial fragment or bacter ial cell in a microplate. The microplate was incubated at 28° C. for 48-72 hours before A595 was measured. Percent growth inhibition was calculated by the following formula:

Percent growth inhibition=Control A595−Test A595/ Control A595

| | |
|---|---|
| Control A595: | A595 of the cultures in the absence VrD1 |
| Test A595: | A595 of the cultures in the presence of VrD1 |

Percent growth inhibition thus obtained was plotted against VrD1 concentrations (µg/ml). The concentration of VrD1 required for 50% inhibition was defined as IC50.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A transformed plant cell comprising a recombinant nucleic acid encoding a heterologous polypeptide that comprises an amino acid sequence at least 80% identical to SEQ ID NO:4, wherein the polypeptide has insecticidal, fungicidal, or bactericidal activity.

2. The transformed plant cell of claim 1, wherein the cell is a dicot plant cell.

3. The transformed plant cell of claim 2, wherein the cell is a tobacco cell.

4. The transformed plant cell of claim 1, wherein the plant is a monocot plant cell.

5. The transformed plant cell of claim 4, wherein the cell is a rice cell.

6. The transformed plant cell of claim 1, wherein the heterologous polypeptide contains SEQ ID NO:4, 6, or 8.

7. A transgenic plant whose genome comprises a recombinant nucleic acid encoding a heterologous polypeptide that comprises an amino acid sequence at least 80% identical to SEQ ID NO:4, wherein the polypeptide has insecticidal, fungicidal, or bactericidal activity.

8. The transgenic plant of claim 7, wherein the plant is a dicot plant.

9. The transgenic plant of claim 8, wherein the plant is a tobacco.

10. The transgenic plant of claim 7, wherein the plant is a monocot plant.

11. The transgenic plant cell of claim 10, wherein the plant is a rice.

12. The transgenic plant of claim 7, wherein the plant is resistant to an insect.

13. The transgenic plant of claim 12, wherein the insect is *Spodoptera litura, Callosobruchus chinensis,* or *Callosobruchus maculatus* (F.).

14. The transgenic plant of claim 7, wherein the plant is resistant to a fungus.

15. The transgenic plant of claim 14, wherein the fungus is *Fusurium oxysoprum* or *F. oxysporum* f.sp.*pisi*.

16. The transgenic plant of claim 7, wherein the plant is resistant to a bacterium.

17. The transgenic plant of claim 16, wherein the bacterium is *Xanthomonas campestris* pv. *Vesicatoria, Staphylococcus epidermidis,* or *Salmonella typhimurium*.

18. The transgenic plant of claim 7, wherein the heterologous polypeptide contains SEQ ID NO:4, 6 or 8.

19. A method of producing a transformed plant cell, the method comprising:

introducing into a plant cell a recombinant nucleic acid that encodes a heterologous polypeptide that comprises an amino acid sequence at least 80% identical to SEQ ID NO:4, and expressing the polypeptide in the cell, wherein the polypeptide has insecticidal, fungicidal, or bactericidal activity.

20. The method of claim 19, wherein the cell is a monocot plant cell or a dicot plant cell.

21. The method of claim 19, wherein the heterologous polypeptide contains SEQ ID NO:4, 6 or 8.

22. A method of producing a transformed plant, the method comprising:

introducing into a plant cell a recombinant nucleic acid that encodes a heterologous polypeptide that comprises an amino acid sequence at least 80% identical to SEQ ID NO:4, expressing the polypeptide in the cell, and cultivating the cell to generate a plant, wherein the polypeptide has insecticidal, fungicidal, or bactericidal activity.

23. The method of claim 22, wherein the plant is a monocot plant or a dicot plant.

24. The method of claim 22, wherein the heterologous polypeptide contains SEQ ID NO:4, 6 or 8.

25. The transformed plant cell of claim 1, wherein the heterologous polypeptide is at least 95% identical to SEQ ID NO:4.

* * * * *